United States Patent
Tate et al.

(10) Patent No.: US 10,463,441 B2
(45) Date of Patent: Nov. 5, 2019

(54) ENDOSCOPE CABINET HAVING PIVOTING ENDOSCOPE SUPPORT ARM AND INTEGRATED AIR SUPPLY

(71) Applicant: TECH STAR MEDICAL, INC., Spring Hill, FL (US)

(72) Inventors: Eric Tate, Brooksville, FL (US); Robert J. Tate, Spring Hill, FL (US)

(73) Assignee: TECH STAR MEDICAL, INC., Spring Hill, FL (US)

( * ) Notice: Subject to any disclaimer, the term of this patent is extended or adjusted under 35 U.S.C. 154(b) by 141 days.

(21) Appl. No.: 15/838,448

(22) Filed: Dec. 12, 2017

(65) Prior Publication Data

US 2019/0175296 A1 Jun. 13, 2019

(51) Int. Cl.
| | | |
|---|---|---|
| *A61B 50/10* | (2016.01) | |
| *H05K 5/00* | (2006.01) | |
| *H05K 5/02* | (2006.01) | |
| *A61B 1/12* | (2006.01) | |
| *A61B 1/015* | (2006.01) | |

(Continued)

(52) U.S. Cl.
CPC .......... *A61B 50/10* (2016.02); *A61B 1/00059* (2013.01); *A61B 1/015* (2013.01); *A61B 1/125* (2013.01); *F26B 9/06* (2013.01); *F26B 21/008* (2013.01); *F26B 25/008* (2013.01); *H05K 5/0017* (2013.01); *H05K 5/0213* (2013.01); *H05K 5/0221* (2013.01); *A61B 2050/105* (2016.02); *A61B 2090/0803* (2016.02)

(58) Field of Classification Search
CPC ........ F26B 25/008; F26B 21/008; F26B 9/06; A61B 50/10; A61B 1/00059; A61B 1/125; A61B 1/015; A61B 2050/105; A61B 2090/0803; H05K 5/0213; H05K 5/0221; H05K 5/0017

See application file for complete search history.

(56) References Cited

U.S. PATENT DOCUMENTS

| | | |
|---|---|---|
| 5,534,221 A | 7/1996 | Hillebrenner et al. |
| 6,814,932 B2 | 11/2004 | Hlebovy et al. |

(Continued)

FOREIGN PATENT DOCUMENTS

| | | |
|---|---|---|
| EP | 1290983 | 3/2003 |
| JP | 2007-313113 | 12/2007 |

(Continued)

OTHER PUBLICATIONS

Anonymous, Wassenburg Medical, Wassenburg® SC320, "Excellent Ergonomics and Workflow," Product Brochure, 2016, 2 pages.

*Primary Examiner* — Jessica Yuen
(74) *Attorney, Agent, or Firm* — Allen, Dyer, Doppelt + Gilchrist, P.A.

(57) ABSTRACT

An endoscope storage cabinet includes a plurality of spaced endoscope hangers, each having a longitudinal support arm pivotably mounted at a wall of the cabinet and articulate downward toward the front of the cabinet. A valve block is supported at the upper end of each support arm and includes at least one air flow channel communicating with an air channel of the support arm. An endoscope valve interface on the valve block connects to at least one air orifice on the valve block and at least one valve of an endoscope control body and is configured to suspend the endoscope in spaced relation to other supported endoscopes and permit filtered air to flow through at least one internal channel of the endoscope to facilitate drying.

18 Claims, 10 Drawing Sheets

(51) Int. Cl.
*F26B 9/06* (2006.01)
*F26B 21/00* (2006.01)
*F26B 25/00* (2006.01)
*A61B 1/00* (2006.01)
*A61B 90/00* (2016.01)

(56) References Cited

U.S. PATENT DOCUMENTS

| | | |
|---|---|---|
| 8,414,471 B2 | 4/2013 | Mandava et al. |
| 8,591,668 B2 | 11/2013 | Pieroni et al. |
| 8,992,416 B2 | 3/2015 | Mandava et al. |
| 9,566,127 B1 | 2/2017 | Guezuraga et al. |
| 2014/0097954 A1 | 4/2014 | Mandava et al. |
| 2017/0205949 A1 | 7/2017 | Uchida et al. |

FOREIGN PATENT DOCUMENTS

| | | |
|---|---|---|
| JP | 2008054861 | 3/2008 |
| WO | 98/25569 | 6/1998 |
| WO | 2009/062490 | 5/2009 |
| WO | 2009/153481 | 12/2009 |
| WO | 2010/136093 | 12/2010 |
| WO | 2015/057057 | 4/2015 |
| WO | 2017/153414 | 9/2017 |

ENDOSCOPE CABINET HAVING PIVOTING ENDOSCOPE SUPPORT ARM AND INTEGRATED AIR SUPPLY

FIELD OF THE INVENTION

The present invention relates to cabinets for storing medical equipment, and more particularly, this invention relates to an endoscope storage cabinet.

BACKGROUND OF THE INVENTION

Flexible endoscopes are used in numerous and different medical procedures, including gastroenterology, and manufactured by different companies. Examples of flexible endoscopes include a flexible gastroscope, colonoscope, duodenoscope (ERCP), and sigmoidoscope. Another related but somewhat different flexible endoscope is an inter bowel endoscope used in small bowel and intestinal procedures.

Endoscopes are complex and expensive medical instruments and may include an internal light source to view hidden parts inside the human body. However, even with these benefits, endoscopes have been traced to many healthcare-associated disease outbreaks due to improper cleaning after use, followed by subsequent use in a new patient. Flexible endoscopes, especially by virtue of the different body cavities they are used to visualize, acquire high levels of microbial contamination and bioburden during use, and thus, proper cleaning between uses is essential. Cleaning flexible endoscopes, however, can be challenging because the devices are usually very heat-sensitive and cannot be sterilized under high heat conditions. Instead, flexible endoscopes must be properly cleaned following each use by hand and then subjected to high-level disinfection.

Usually a flexible endoscope is pre-cleaned immediately after use and wiped down with a detergent-soaked cloth. Detergent often is aspirated with air through a suction channel. The endoscope is flushed and then channel brushed, especially in those endoscopes having elevators or auxiliary-water feeding. A water-resistant cap is attached to protect parts of the videoscope portion of the endoscope. Leakage testing may optionally occur followed by manual cleaning in a tank with a prepared detergent solution. External surfaces are cleaned by brushing. The device is aspirated with detergent, followed by soaking and rinsing and then flushed with clean water through all channels, followed by flushing air through the channels. Excess moisture is removed from the endoscope and any cleaning accessories. During this process, the endoscope may be manually transported to a washer/disinfector for a 20 to 30 minute cleaning to produce a clean and highly disinfected flexible endoscope. Upon completion of that process, the flexible endoscope is usually manually transported and placed inside a storage cabinet, which may also operate as a drying cabinet for recently processed endoscopes.

There are many different types of endoscope storage cabinets available for use. Most provide an ambient ventilated inner chamber where the flexible endoscopes are stored. HEPA filtered air is blown around the endoscopes to dry their exterior surfaces. Often separate tubes are connected to the different valve ports on the control (or valve) body of the endoscope to blow air into the various channels and facilitate their drying. The holding capacity of these cabinets vary, but range from holding 6, 10, 16, or 20 endoscopes. They usually have some type of lighting and a locking mechanism on the cabinet door together with a system to keep track of the endoscopes and any associated data.

Often the endoscopes are hung on hooks or held in position within the cabinet by some other mechanism that usually is adjacent to or positioned on the rear interior wall of the cabinet. In those storage cabinets that do not provide the capacity for air flow into the various channels of the flexible endoscope, the endoscope cabinet should include a source of HEPA filtered air to provide a positive air pressure and accommodate air circulation around the endoscopes. To enhance drying and minimize the chance of bacterial build-up within the endoscope, they are usually stored with the valves opened and any removable parts detached. The endoscope is stored so that the removable parts can be tracked with the specific endoscope and maintained in close proximity to the endoscope to which they belong. Usually some type of endoscope tracking system identifies which flexible endoscope is to be processed and used next and when it is installed or removed from the cabinet.

Although many endoscope storage cabinets provide for ambient HEPA air to be circulated around the outer surface of the endoscopes, more recent cabinet design have the capacity to pump air through the various endoscope channels. This helps keep the scope dry, and from a microbiology perspective aids in preventing moisture build-up. The absence of moisture prevents replication of bacteria and prevents the formation of a biofilm. One problem associated with some storage cabinets that do circulate air through various endoscope channels is those endoscopes are coiled and touch the base of the cabinet. Those locations of contact act as microbial growth centers. Even if the endoscopes are hung vertically where the distal tip hangs freely in a well-ventilated, clean area, a portion of the scope such as the control body may still be clamped tightly creating a possible bacterial growth center while multiple identification tags or labels that are affixed to the endoscope near the control body may add to possible contamination issues.

Even those cabinet designs, however, that minimize contact of the endoscope with the interior surfaces of the cabinet and provide a good flow of HEPA filtered air around the scope and within its channels are often designed such that it is difficult to install and remove endoscopes from the cabinet. Endoscopes are long and usually include a light guide connector connected to a flexible light guide tube, which in turn, connects to the control body (valve body). The insertion tube extends from the control body, which may include suction and air/water valves and distal from those valves could be an instrument channel port, thus adding to the overall length. When hanging vertically in a cabinet, the control body is often positioned at least 6 feet from the floor of the cabinet. This height often makes the control body inaccessible or difficult to reach. This is especially critical if tubes have to be connected to valve ports on the control body and other portions of the endoscope must be positioned correctly on a hangar or clamp. Many staff members must step or reach up to grasp the head or control body of the endoscope. Some individuals may even have to stand on a step stool to retrieve the endoscope, inviting a host of potential staff injuries.

SUMMARY OF THE INVENTION

This summary is provided to introduce a selection of concepts that are further described below in the detailed description. This summary is not intended to identify key or essential features of the claimed subject matter, nor is it intended to be used as an aid in limiting the scope of the claimed subject matter.

An endoscope storage cabinet includes an enclosed structure having a plurality of walls defining an inner area, including in a non-limiting example a rear inner wall and a cabinet door allowing access to the inner area. A plurality of spaced endoscope hangers are within the inner area. Each endoscope hanger comprises a longitudinal support arm having an upper end on which an endoscope is supported and a lower end pivotably mounted at a wall within the cabinet, and in a non-limiting example, at a rear inner wall allowing the support arm to articulate downward toward the front of the cabinet. An air channel extends from the lower to the upper end through which filtered air flows. A valve block is supported at the upper end of the support arm and includes at least one air flow channel communicating with the air channel of the support arm. At least one air orifice is on the valve block. An endoscope valve interface is on the valve block and includes an interface orifice that communicates with the at least one air orifice on the valve block. The valve interface engages at least one valve of an endoscope control body and is configured to suspend the endoscope in spaced relation to other endoscopes. Filtered air flows through at least one of the internal channels of the endoscope via the endoscope valve interface to facilitate drying of the internal channel.

A cradle may be mounted at the upper end of each support arm on which a respective valve block is supported. Each cradle may comprise two opposing prongs between which the valve block is supported. Each prong may include a slide mount and each valve block includes opposing sides each having a channel configured to slide over a respective slide mount on the prong to support the valve block on the cradle. Each valve block may include an inner block section having the at least one air flow channel and an outer block section supporting the inner block section. The outer block section has opposing sides, each having the channel configured to slide over a respective slide mount on the prong.

Each support arm may be configured to pivot about 90 degrees toward the front such that the upper end of each support arm articulates downward from about six and one-half feet to about four and one-half feet, facilitating user access to an endoscope. Each endoscope valve interface may comprise silicone configured to engage the endoscope control body and preferably engage at least one valve of the endoscope at the control body. Each valve block may include at least two air orifices and the endoscope valve interface is configured to interface with at least one of suction, air and water valves at the endoscope control body. An air source may provide filtered air and is connected to each pivoting arm to supply filtered air through the air channel to an endoscope supported at the upper end of the support arm. A vent may be positioned within the enclosed structure and connected to the air source and configured to permit air circulation within the inner area over endoscopes and dry the outer surfaces of the endoscopes.

In yet another example, the endoscope storage cabinet may comprise an enclosed structure having a plurality of walls defining an inner area, including a rear inner wall and at least one front cabinet door allowing access to the inner area. The at least one front cabinet door includes a locking mechanism. A plurality of spaced endoscope hangers are within the inner area. Each endoscope hanger includes a longitudinal support arm having an upper end on which an endoscope is supported and a lower end pivotably mounted at the rear inner wall, allowing the support arm to articulate downward toward the front of the cabinet. It includes an air channel extending from the lower end to the upper end through which filtered air flows. A cradle is mounted at the upper end of the support arm. A valve block is supported at the cradle and includes at least one air flow channel communicating with the air channel of the support arm and at least one air orifice on the valve block. An endoscope valve interface is on the valve block and connects to the at least one air orifice on the valve block and at least one valve of an endoscope control body and configured to suspend the endoscope in spaced relation to endoscopes supported on other hangers and permit filtered air to flow through at least one internal channel of the endoscope and facilitate drying of the internal channel. The valve block includes at least two air orifices and the endoscope valve interface is configured to interface with at least one of suction, air and water valves at the endoscope control body.

A controller is connected to the locking mechanism and configured to lock and unlock the at least one cabinet door. A touch display panel is supported by the at least one cabinet door and connected to the controller into which data is entered by a user to lock and unlock the cabinet door and facilitate access to an endoscope. The touch display panel displays identifying information about each endoscope stored within the cabinet. A sensor is located at each endoscope hanger and connected to the controller. Each sensor is configured to sense when an endoscope is inserted for storage or removed and the display panel is configured to display data regarding the removal or insertion of an endoscope.

DESCRIPTION OF THE DRAWINGS

Other objects, features and advantages of the present invention will become apparent from the detailed description of the invention which follows, when considered in light of the accompanying drawings in which.

DETAILED DESCRIPTION

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Figure 1:
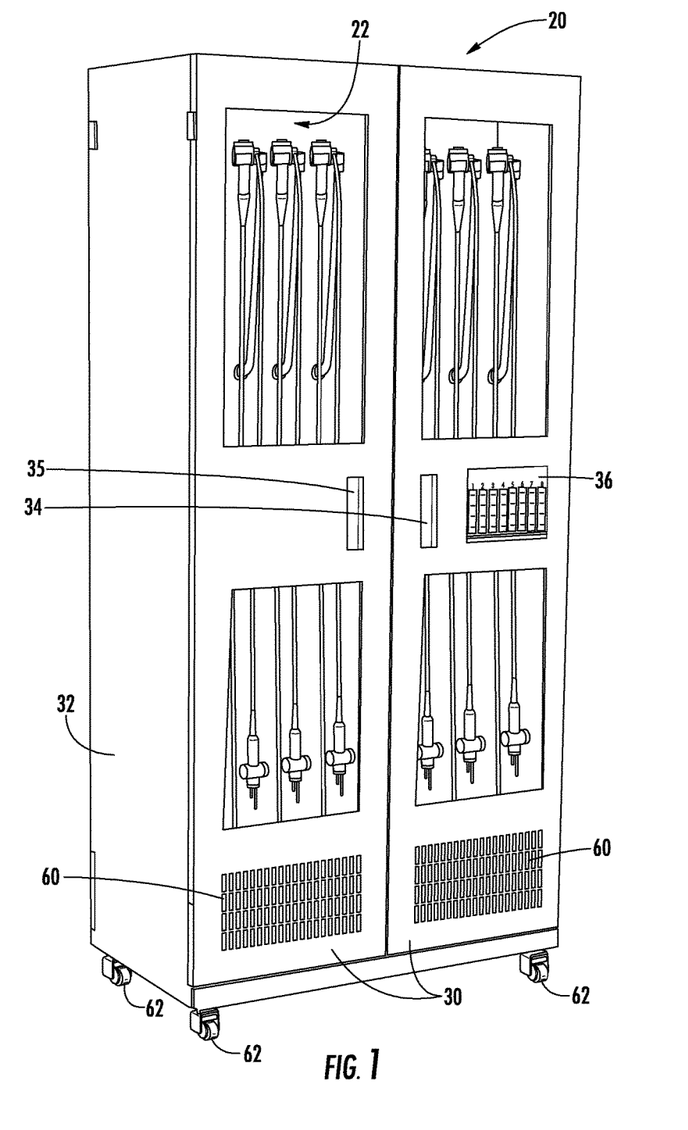
FIG. 1 is a front perspective of the endoscope storage cabinet in accordance with a non-limiting example.
Figure 2:
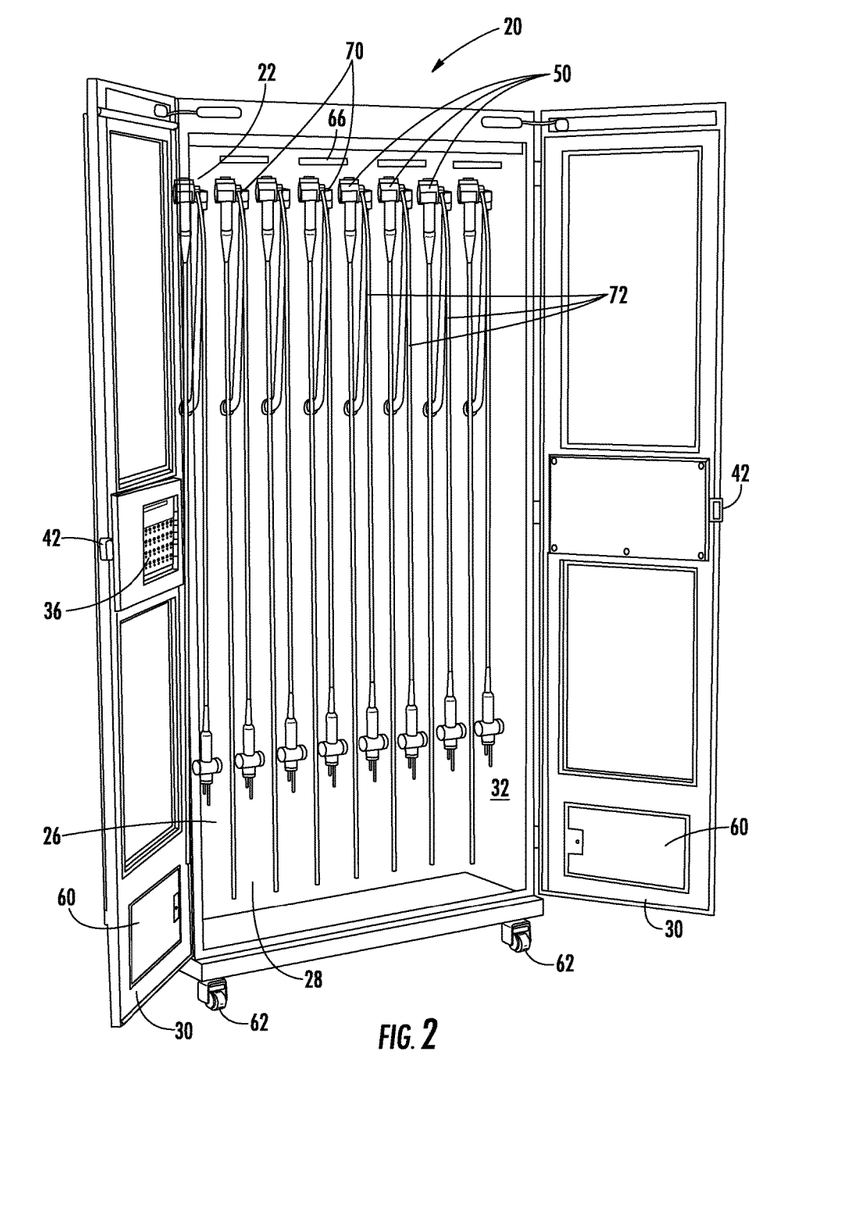
FIG. 2 is a front elevation view of the endoscope storage cabinet of FIG. 1 with the front cabinet doors open and showing a number of stored endoscopes.

Referring now to the figures, and more particularly, FIGS. 1-4, there is illustrated an endoscope storage cabinet illustrated generally at 20 that includes an enclosed structure 22 having a plurality of walls 24 defining an inner area indicated generally at 26 as shown in FIG. 2. The endoscope storage cabinet 20 includes a rear interior wall 28 and a front cabinet door 30 allowing access to the inner area 26. In this embodiment, the storage cabinet 20 includes two front cabinet doors 30 pivotally connected to the front edges of sidewalls 32. The front cabinet doors 30 include handles 34 and one of the doors supports a touch display panel 36, which in this example of FIG. 1 is supported by the right-hand front cabinet door 30. The touch display panel 36 connects to a controller 38, for example, supported in the rear section of the display cabinet shown with open rear cabinet doors 40 in FIG. 4. The front cabinet doors 30 include a locking mechanism 42 connected to the controller 38, which is configured to lock and unlock the front cabinet doors 30. Data may be entered by a user via the touch display panel 36 to lock and unlock the front cabinet doors 30 via the locking mechanism 42 and facilitate access to an endoscope. The touch display panel 36 may display identifying information of each endoscope stored within the cabinet.

Figure 3:
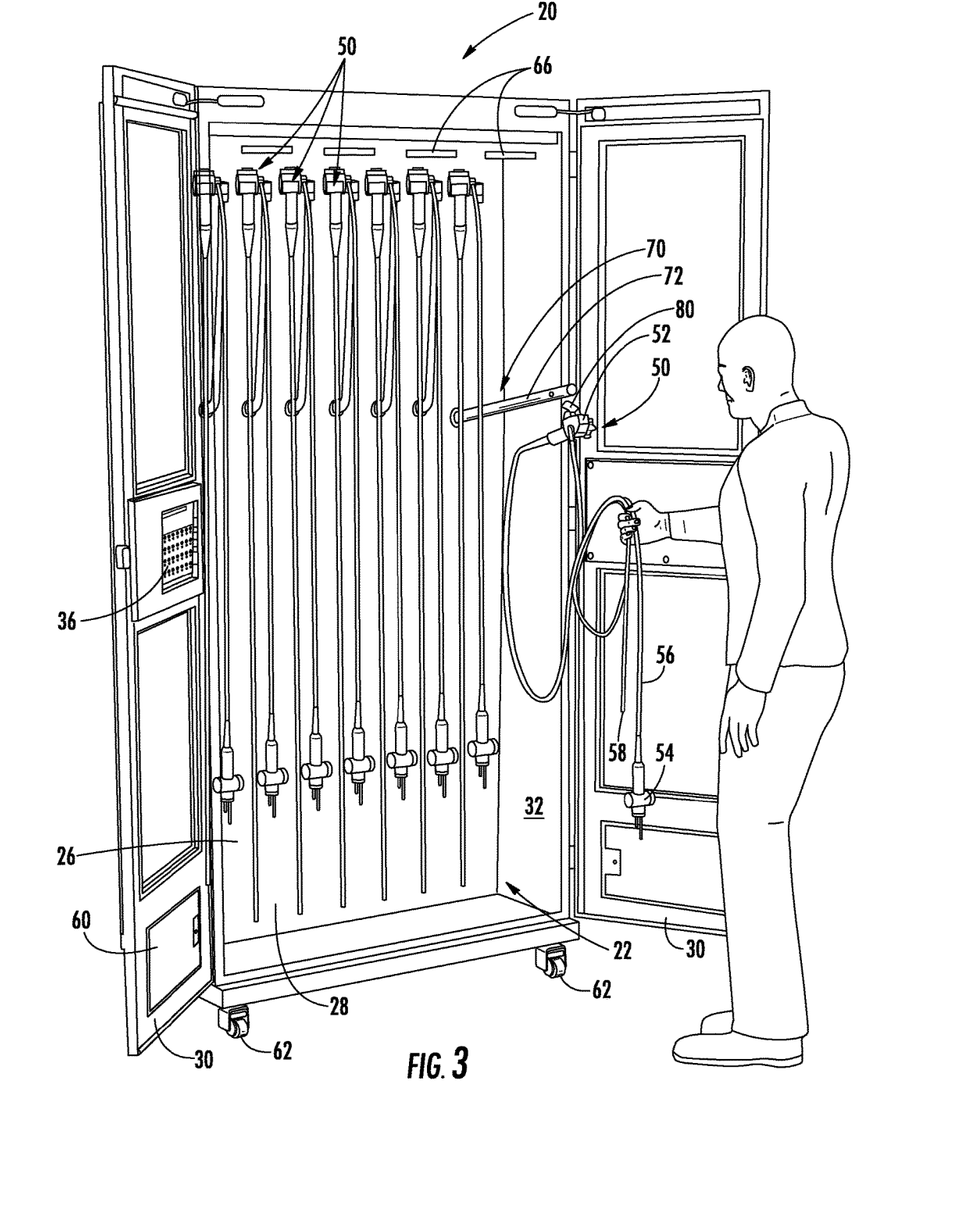
FIG. 3 is a front perspective view of the endoscope storage cabinet of FIGS. 1 and 2 and showing a user removing an endoscope from a support arm.
Figure 4:
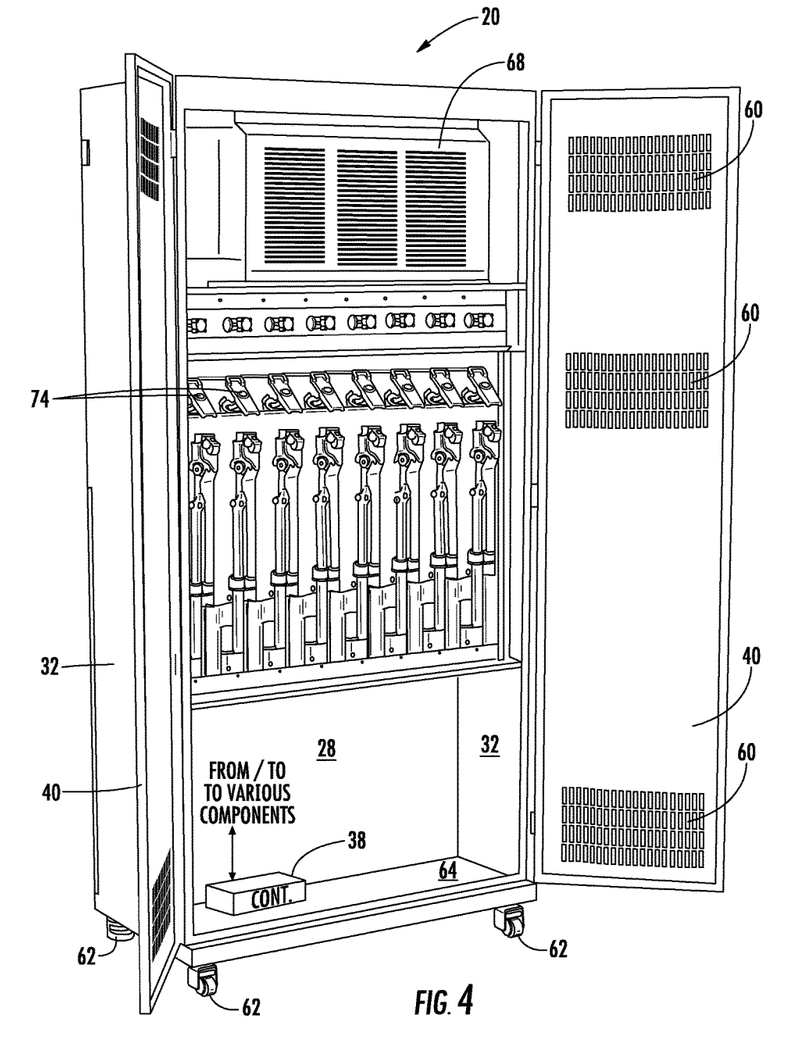
FIG. 4 is a rear perspective view of the endoscope storage cabinet with the rear cabinet doors open.
Figure 13:
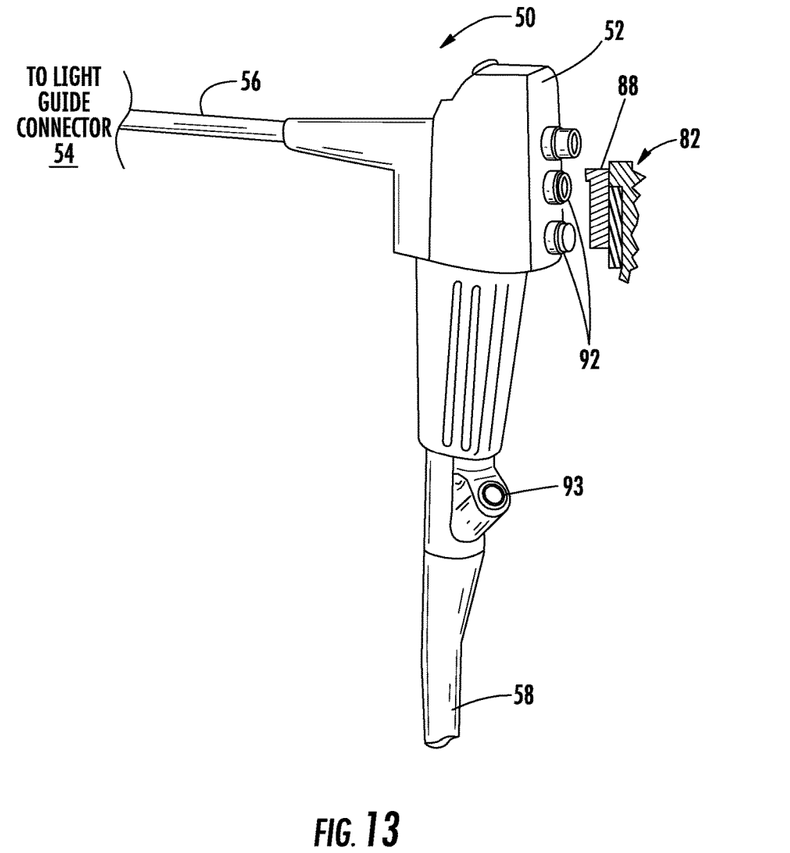
FIG. 13 is a partial fragmentary and sectional view showing in sectional view the endoscope valve interface as a portion of the valve block and how they engage valves on the endoscope control body.

As shown in FIG. 2, eight flexible endoscopes generally shown at 50 are stored in the endoscope storage cabinet. Each flexible endoscope 50 includes the basic endoscope components as shown in FIGS. 3 and 13 of a control (or valve) body 52, a light guide connector 54 connected via a light guide cable 56 to the control body 52, and the insertion tube 58. Both front and rear cabinet doors 30,40 include air vents 60 to enhance air circulation. Rollers such as castors 62 are positioned at each corner on the outside surface of the bottom wall of the cabinet 20 corresponding to the floor 64. This allows a staff member to facilitate movement of the storage cabinet 30 by rolling it into a desired position. The cabinet 20 includes at least one internal air vent 66 and preferably a number of internal air vents such as positioned in the rear inner wall 28 and connected to an air source 68 (FIG. 4) to provide HEPA filtered air flow through the vents, which are configured to permit air circulation within the inner area 26 and over endoscopes, and thus, dry the outer surfaces of the endoscopes.

As best shown in FIGS. 2 and 3, a plurality of spaced endoscope hangers 70 are positioned within the inner area 26. In the example shown in FIGS. 2 and 3, eight endoscope hangers 70 are positioned in the inner area 26. Each endoscope hanger 70 includes a longitudinal support arm 72 having an upper end 72a on which an endoscope is supported and a lower end 72b (FIG. 6) pivotably mounted at the rear inner wall 28 allowing the support arm 72 to articulate downward toward the front of the storage cabinet 20. In an example, the pivoting support arm 72 extends through an opening in the rear inner wall 28 and is connected at the rear side of the rear inner wall 28 of the storage cabinet 20 at a pivot support member 74 shown best in FIG. 4, which mounts the support arm for pivoting movement. Each longitudinal support arm 72 has an air channel 76 (FIG. 6) extending from the lower end 72b to the upper end 72a through which filtered air flows as provided by the air source 68 shown in FIG. 4. Air supply tubes (not shown in detail) could extend from the air source 68 to the pivot support member 74 and connect to the air channel 76 and provide air flow into the air channel extending from the lower to the upper end of the support tube. The air source 68 preferably provides a source of HEPA-filtered air in this example.

Figure 6:
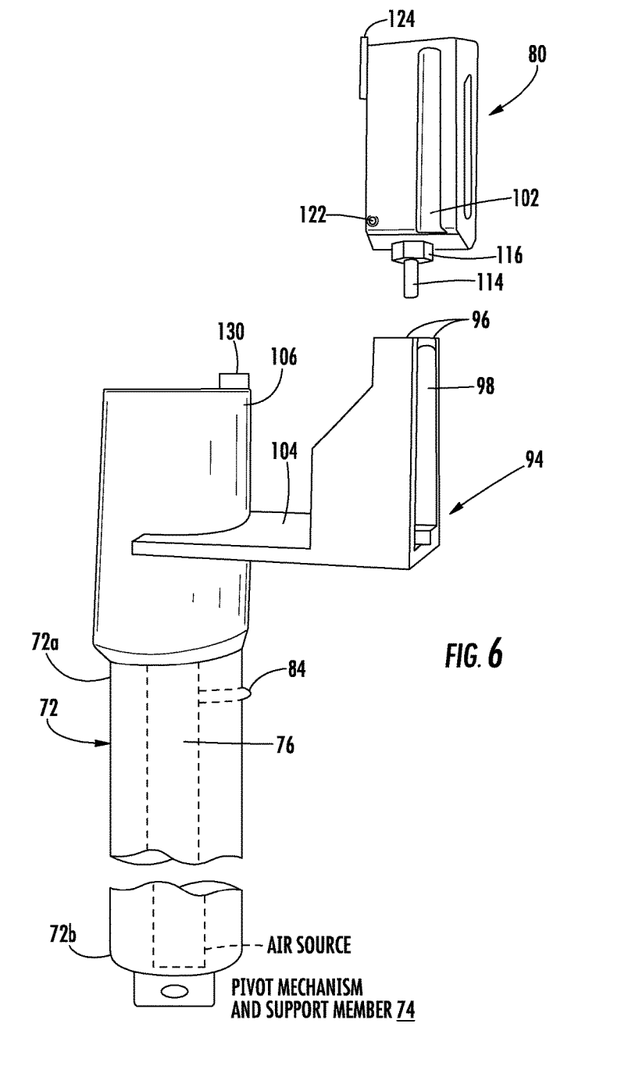
FIG. 6 is a side perspective view showing the cradle and valve block.
Figure 9:
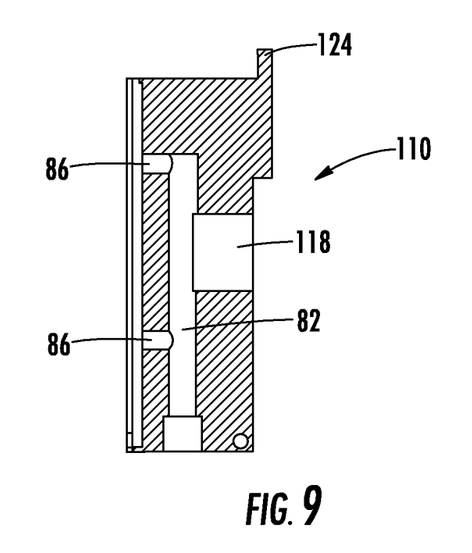
FIG. 9 is a sectional view of the inner block section shown in FIG. 8.

A valve block 80 (FIGS. 6 and 7) is supported at the upper end 72a of each support arm 72 and includes at least one air flow channel 82 (FIG. 9) communicating with the air channel 76 in the support arm 72 as best shown in FIG. 6 where a tube may connect from the valve block to an air fitting 84 on the support arm 72, which communicates with the air channel 76. There is at least one valve block air orifice 86, and in the illustrated example, there are two air orifices (FIG. 9). An endoscope valve interface 88 (FIGS. 7 and 13) is supported by the valve block 80 and includes interface air orifices 90 that also are in communication with the valve block air orifices 86 and engage endoscope valves 92 at the endoscope control or valve body 52 such as shown in FIG. 13. The valve interface 88 is also configured to suspend the endoscope 50 in spaced relation to the other endoscopes supported on other endoscope hangers 70 and permit filtered air to flow through at least one internal channel of the endoscope, and in this example, the different internal channels of the endoscope and facilitate drying of the internal channels.

Figure 5:
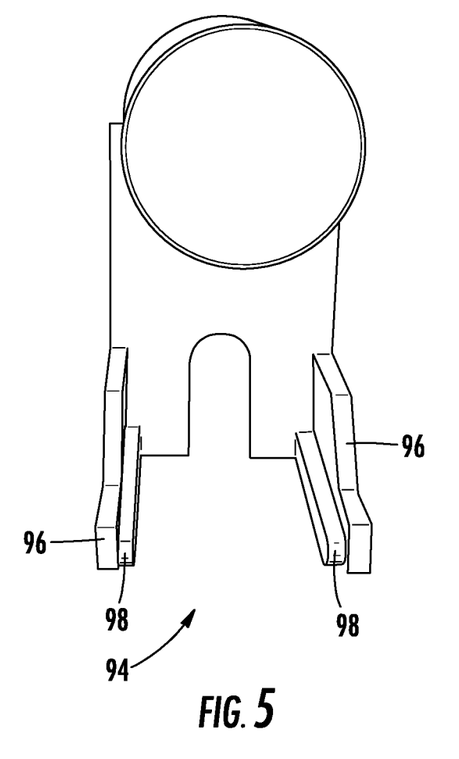
FIG. 5 a top perspective view of the cradle.

A cradle 94 is mounted at the upper end 72a of each support arm 72 and on which a respective valve block 80 is supported. In the example shown in FIGS. 5 and 6, each cradle 94 includes two opposing prongs 96 between which the valve block 80 is supported. Each prong 96 includes a longitudinal slide mount 98, such as a longitudinally extending protruded surface formed on the inside surface of each prong. Each valve block 80 includes opposing sides each having a slotted channel 102 configured to receive the respective slide mount 98 on the prong 96 and support the valve block 80 within the cradle 94. The two opposing prongs 96 are attached by a flange 104 to a cylindrical support member 106, which attaches onto the end of the longitudinal support arm 72 as shown in FIGS. 3 and 6, where in FIG. 3 a staff member has pivoted downward the support arm to gain access to a stored endoscope. As illustrated, each support arm 72 is configured to pivot about 90 degrees toward the front of the cabinet and extend out from the front such that the upper end 72a of each support arm articulates downward from about 6½ feet to about 4½ feet, facilitating user access to an endoscope.

Referring now to FIGS. 8-12, there are illustrated details of an example construction of the valve block 80, which includes an inner block section 110 having the flow channel 82 and valve block air orifices 86 and an outer block section 112 supporting the inner block section. The outer block section 112 has opposing sides each having the slotted channel 102 configured to receive a respective slide mount 98 formed on the prong 96. The inner block section 110 includes an air supply fitting 114 (FIG. 6) that is attached by a fastener 116, such as a nut, into the air channel 82 to communicate with the two orifices 86. A larger orifice 118 on the opposing side can be used to supply air via a fitting at that orifice to other areas, such as on the endoscope control body 52 via the fitting (not shown) that may be screwed as an example into the larger orifice 118.

Figure 7:
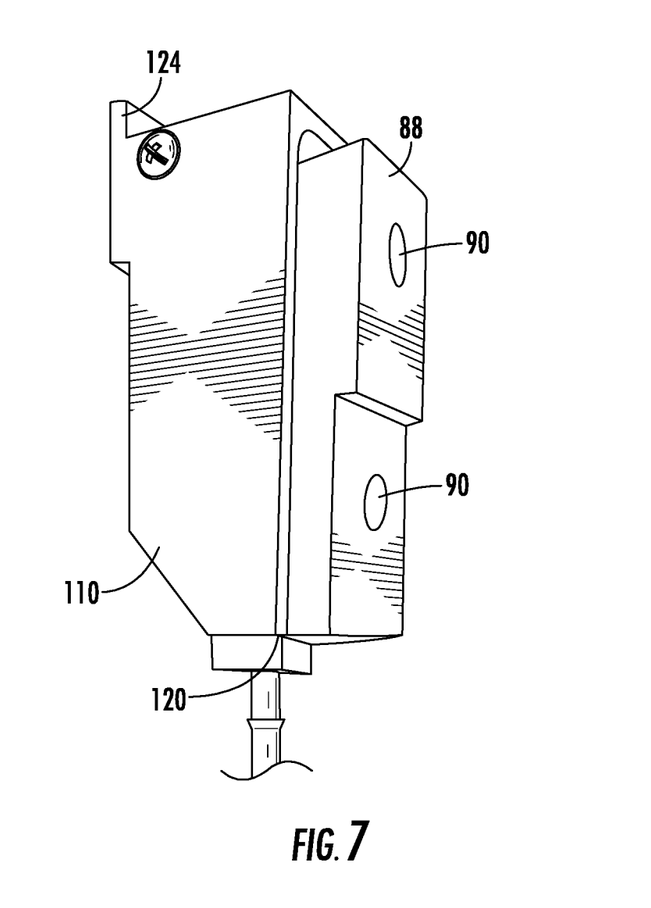
FIG. 7 is a side perspective view showing the valve block and endoscope valve interface.
Figure 8:
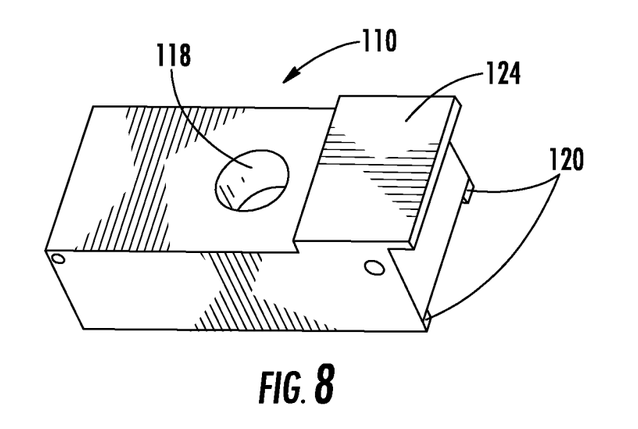
FIG. 8 is a perspective view of the inner block section of the valve block.

As shown in FIG. 8, the lower portion of the inner block section includes channels 120 or slots on either side that receive the endoscope valve interface 88 as shown in the example of FIG. 7. The valve interface 88 slides into the formed channel or slot 120 and the orifices 90 in the valve interface 88 align with the valve block air orifices 86. Each endoscope valve interface 88 could be formed of silicone and configured to engage the endoscope control body 52 at its valves such as at least one of the suction, air, and water valves (FIG. 13) and create an airtight fit. Air is blown via the support tube and passes from the valve body 80 and via the endoscope valve interface 88 into the various channels of the endoscope while also supporting the endoscope in one example in a frictional fit at the valve interface 88. Of course, there could be other fixtures, supports or devices that assist in supporting the endoscope, for example, by having support members on the prongs 96 that attach to the endoscope control body and aid in securing the endoscope control body on the cradle 94.

FIG. 9 shows that the larger orifice 118 is opposite the orifices 86 that engage with the endoscope valve interface and a fitting could be inserted within the large orifice to block the flow of air or permit air flow via a tube into, for example, the biopsy valve 93 or other valves located on the endoscope control body (FIG. 13). In some instances, vacuum could be drawn via vacuum orifices formed on the valve body and endoscope valve interface to help secure the endoscope valve interface securely with the endoscope depending on its design. One aspect is that different endoscope valve interfaces 88 can be slid onto the inner block section 110 via the grooves or slots 120 to accommodate different styles of endoscopes via differently designed and configured endoscope valve interfaces. The endoscope valve interfaces 88 can be discarded after each use.

Figure 10:
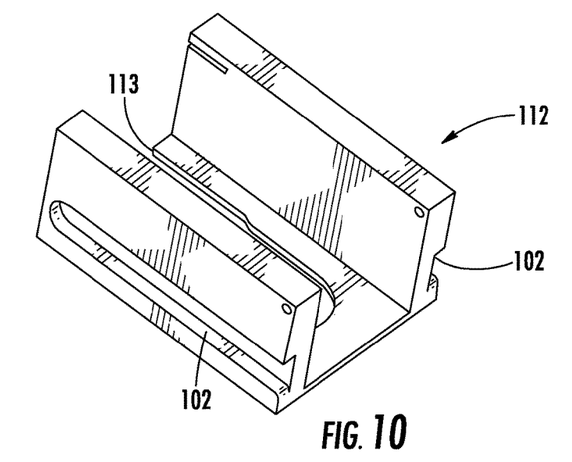
FIG. 10 is a perspective view of the outer block section that receives the inner block section shown in FIG. 8.
Figure 11:
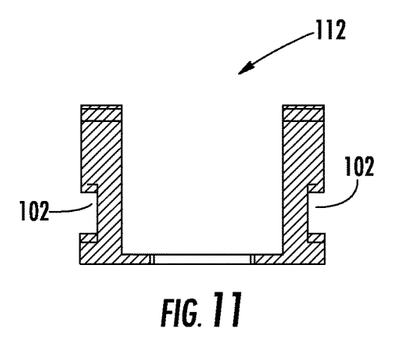
FIG. 11 is a sectional view of the outer block section shown in FIG. 10.
Figure 12:
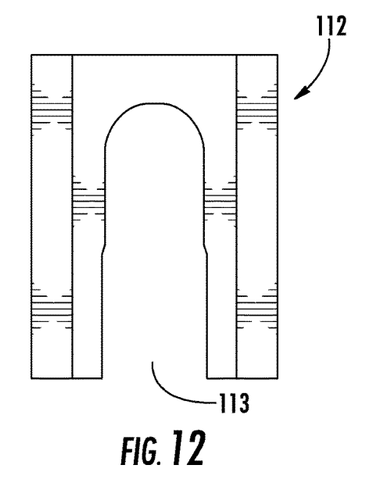
FIG. 12 is a top plan view of the outer block section shown in FIG. 10.

The support arm 72 can be made from different materials, including hard plastic or metallic material, such as aluminum or other materials. The storage cabinet 20 typically may be made from sheet metal, plastic, or other similar materials, although sheet metal for the cabinet and a resistant glass for the front cabinet doors 30 is preferred. The inner block section 110 can be made of plastic or a metallic material such as lightweight aluminum and may be molded or machined. The outer block section 112 is H-shaped as shown in FIGS. 10 and 11 and may be made from similar materials as the inner block section. It includes the side walls having the slotted channel 102 and a base with a U-shaped slot 113 through which the valve interface 88 extends from the inner block section 110. The sizes of these components can vary depending on the type of endoscope that is to be supported, but generally the valve block 80 is at most no more than a few inches square, and in one example, about an inch and a half in length and about an inch in width. The inner block section 110 and outer block section 112 can be secured to each other via a fastener 122 such as shown in FIG. 6. The inner block section 110 includes a flange 124 (FIGS. 6-9) that can help retain the sections together or help hold the endoscope on the cradle when the endoscope is supported within the cabinet. The outer block section 112 includes the slot or grooves 120 as shown in FIG. 12 through which the endoscope valve interface 88 is received and extends from the inner block section.

It is also desirable to track each flexible endoscope 50 as it is inserted and removed from the storage cabinet 20. In one example, a sensor 130 is positioned at each endoscope hanger and connected to the controller 38, such as the sensor shown in FIG. 6. Each sensor 130 is configured to sense when an endoscope is inserted for storage or removed. The touch display panel 36 is configured to display data regarding the removal or insertion of an endoscope 50. Also, a user can identify and insert data regarding each endoscope via the touch display panel 36 and maintain data on each stored endoscope and track time periods of how long an endoscope has been stored within the storage cabinet 20. The design of each sensor can vary, but in one example, could be a light emitting diode with a receiver where the light is broken when the endoscope is inserted or could include radio frequency or light devices that use reflection from the endoscope when inserted. Many other designs are possible. Various barcodes could be used and scanners operated with the touch display panel to help keep track of the endoscopes.

It is possible to use RFID technology on both user tracking and endoscope tracking as well as other possible data inputs as identified before. For example, many facilities now use RFID badging for employee tracking and access capabilities. This RFID badging technology may be integrated with the endoscope cabinet for faster and more simple access for employees. Many endoscopes on the market now have RFID chips built in that can be integrated with the endoscope cabinet to ease the employees' data entry to track the endoscope. For example, the system at the endoscope cabinet could use a tracking assembly to track which employee enters their badge number or read the badge for automatic access and then track which endoscope is inserted or removed through the same RFID system. The system may use a passive or active type of tag depending on requirements. One advantage over bar codes is the RFID tag can be read with a reader even though the device may not be visible.

The endoscope storage cabinet 20 could include RFID signal receiving devices or antennae placed in an appropriate position within the cabinet and connected to the controller 38. One possible area could be the lower area of the cabinet for placing the antennae or other devices. It is possible to have a drip pan also in the lower section of the cabinet that collects and drains the fluid from recently cleaned endoscopes. Alerts could be provided based on tracked endoscopes. If an endoscope has been removed for an extended period of time and has not been checked back into the cabinet, this indicates it should have been cleaned and returned by a certain period of time and an alarm sent. Alarms could be sent if the endoscope had been stored in the cabinet for an excessive time period. The alarms could be signals sent to wireless phones or a central control console at the establishment such as a hospital. Alarms could be in the form of email messages. The endoscopes could have passive or active RFID tags that are planar configured and attached on part of the valve body or other locations on an endoscope.

The amount of filtered air passing through the storage cabinet 20 can vary as well as the amount of air flowing within the endoscope channels. A positive cabinet pressure is maintained via the HEPA filter and air source 68 to protect the endoscopes from environmental contaminants during loading and unloading of instruments. The air source 68 may include an air compressor to deliver the dry HEPA-filtered air. If manual or automatic barcode readers are used in association with the touch display panel 36, staff members may record an endoscope identifier (ID), an operator identifier, case-specific data, entry/removal times, and other data for each endoscope. The locked front cabinet door 30 protects the endoscope inventory and the touch display panel 36 can determine different cycles. A printer can be connected to the controller and associated with the storage cabinet 20 to print documentation and reports or screen shots from the touch display panel 36.

An electrical supply could include a standard 120 volt AC power supply with a power input of about 120 watts in one example. The vertical hanging of each endoscope via the endoscope hangers 70 is desirable since the cabinet design as described prevents the different endoscopes from touching and damaging each other and maintains their shape without damaging coil memory, while eliminating any chance of water draining onto other endoscopes. The HEPA filter could use a three-phase filtration media to remove as much as 99.7% of particulates. In one example, 304 stainless steel can be used in the cabinet construction with tempered glass windows in the hinged front cabinet doors. The cabinet may include internal cabinet LED lighting and a drip pan.

The controller 38 and touch display panel 36 may be used together to maintain records related to the endoscope processing such as the date and time of storage and removal, the identity of the endoscope, and track any accessories that may be stored with the endoscope, while also verifying any endoscope cleaning and any results of that cleaning and subsequent testing, if any, the identity of any persons that have used or will use the endoscopes, different lot numbers and processing solutions, the disposition of defective items or equipment, and maintenance of the endoscope, its accessories, its processing equipment, and its water systems. Different records may be related to use of endoscope procedures that include the date and time, the identity of a patient, the procedure, the identity of any practitioners, and any other associated recordkeeping data. Although storage times for flexible endoscopes vary, it is possible to store an endoscope in the storage cabinet up to almost two months after processing when proper air circulation occurs within the cabinet itself and air is circulated through the endoscope channels.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An endoscope storage cabinet, comprising:
   an enclosed structure having a plurality of walls defining an inner area, including a cabinet door allowing access to the inner area;
   a plurality of spaced endoscope hangers within the inner area, each endoscope hanger comprising,
      a longitudinal support arm having an upper end on which an endoscope is supported and a lower end pivotably mounted at a wall allowing the support arm to articulate downward toward the front of the cabinet, and having an air channel extending from the lower to the upper end through which filtered air flows; and
      a valve block supported at the upper end of the support arm and including at least one air flow channel communicating with the air channel of the support arm and at least one air orifice on the valve block, and an endoscope valve interface on the valve block that connects to the at least one air orifice on the valve block and at least one valve of an endoscope at the endoscope control body and configured to suspend the endoscope in spaced relation to endoscopes supported on other endoscope hangers and permit filtered air to flow through at least one internal channel of the endoscope and facilitate drying of the internal channel.

2. The endoscope storage cabinet according to claim 1 further comprising a cradle mounted at the upper end of each support arm on which a respective valve block is supported.

3. The endoscope storage cabinet according to claim 2 wherein each cradle comprises two opposing prongs between which the valve block is supported.

4. The endoscope storage cabinet according to claim 3 wherein each prong includes a slide mount and each valve block includes opposing sides each having a channel configured to receive a respective slide mount to support the valve block on the cradle.

5. The endoscope storage cabinet according to claim 4 wherein each valve block includes an inner block section having an air flow channel and an outer block section supporting the inner block section, said outer block section having opposing sides each having the channel configured to receive a respective slide mount.

6. The endoscope storage cabinet according to claim 1 wherein each support arm is configured to pivot about 90 degrees toward the front such that the upper end of each support arm articulates downward from about six and a half feet to four and a half feet facilitating user access to an endoscope.

7. The endoscope storage cabinet according to claim 1 wherein each endoscope valve interface comprises silicone configured to engage the control body of an endoscope and engage a valve of the endoscope to facilitate air flow therein.

8. The endoscope storage cabinet according to claim 1 wherein each valve block includes at least two air orifices and the endoscope valve interface is configured to interface with at least one of suction, air and water valves at the endoscope control body.

9. The endoscope storage cabinet according to claim 1 including an air source providing filtered air and connected to each pivoting arm to supply filtered air through the air channel to an endoscope supported at the upper end of the support arm.

10. The endoscope storage cabinet according to claim 9 further comprising a vent positioned within the enclosed structure and connected to the air source and configured to permit air circulation within the inner area over endoscopes and dry the outer surfaces of the endoscopes.

11. An endoscope storage cabinet, comprising:
    an enclosed structure having a plurality of walls defining an inner area, including a rear inner wall and at least one cabinet door allowing access to the inner area, said at least one cabinet door including a locking mechanism;
    a plurality of spaced endoscope hangers within the inner area, each endoscope hanger comprising,
       a longitudinal support arm having an upper end on which an endoscope is supported and a lower end pivotably mounted at the rear inner wall allowing the support arm to articulate downward toward the front of the cabinet, and having an air channel extending from the lower to the upper end through which filtered air flows;
       a cradle mounted at the upper end of the support arm and a valve block supported at the cradle and including at least one air flow channel communicating with the air channel of the support arm and at least two air orifices on the valve block, and an endoscope valve interface on the valve block that communicates with the at least two air orifices on the valve block and at least one of suction, air and water valves of an endoscope control body, wherein the endoscope valve interface is configured to suspend the endoscope in spaced relation to endoscopes supported on other hangers and permit filtered air to flow through at least one internal channel of the endoscope and facilitate drying of the internal channel;

a controller connected to the locking mechanism and configured to lock and unlock the at least one cabinet door;

a touch display panel supported by the at least one front door and connected to the controller into which data is entered by a user to lock and unlock the front door and facilitate access to an endoscope, wherein said touch display panel displays identifying information of each endoscope stored within the cabinet; and a sensor at each endoscope hanger and connected to said controller, wherein each sensor is configured to sense when an endoscope is inserted for storage or removed and said touch display panel is configured to display data regarding the removal or insertion of an endoscope.

12. The endoscope storage cabinet according to claim 11 wherein each cradle comprises two opposing prongs between which the valve block is supported.

13. The endoscope storage cabinet according to claim 12 wherein each prong includes a slide mount and each valve block includes opposing sides each having a channel configured to receive a respective slide mount to support the valve block on the cradle.

14. The endoscope storage cabinet according to claim 13 wherein each valve block includes an inner block section having an air flow channel and an outer block section supporting the inner block section, said outer block section having opposing sides each having the channel configured to receive a respective slide mount.

15. The endoscope storage cabinet according to claim 11 wherein each support arm is configured to pivot about 90 degrees such that the upper end of each support arm articulates downward from about six and a half feet to four and a half feet facilitating user access to an endoscope.

16. The endoscope storage cabinet according to claim 11 wherein each endoscope valve interface comprises silicone configured to engage the control body of an endoscope and engage a valve of the endoscope to facilitate air flow there.

17. The endoscope storage cabinet according to claim 11 including an air source providing filtered air and connected to each pivoting arm to supply filtered air through the air channel to an endoscope supported at the upper end of the support arm.

18. The endoscope storage cabinet according to claim 11 further comprising a vent positioned within the enclosed structure and connected to the air source and configured to permit air circulation within the inner area over endoscopes and dry the outer surfaces of the endoscopes.

* * * * *